US012599440B2

(12) United States Patent
Wu et al.

(10) Patent No.: US 12,599,440 B2
(45) Date of Patent: Apr. 14, 2026

(54) ADJUSTABLE MARKER REFERENCE DEVICE

(71) Applicant: Point Robotics Medtech Inc., Hsinchu County (TW)

(72) Inventors: Chao-Wei Wu, Hsinchu County (TW); Ting-Yun Fang, Hsinchu County (TW)

(73) Assignee: Point Robotics Medtech Inc., Hsinchu County (TW)

( * ) Notice: Subject to any disclaimer, the term of this patent is extended or adjusted under 35 U.S.C. 154(b) by 254 days.

(21) Appl. No.: 18/599,122

(22) Filed: Mar. 7, 2024

(65) Prior Publication Data

US 2025/0120769 A1      Apr. 17, 2025

(30) Foreign Application Priority Data

Oct. 12, 2023      (TW) ................................. 112138833

(51) Int. Cl.
*A61B 34/20*      (2016.01)
(52) U.S. Cl.
CPC ...... *A61B 34/20* (2016.02); *A61B 2034/2072* (2016.02)

(58) Field of Classification Search
CPC ............ A61B 34/20; A61B 2034/2072; A61B 2034/2055
See application file for complete search history.

(56) References Cited

U.S. PATENT DOCUMENTS 7,840,256 B2      11/2010   Lakin et al.

*Primary Examiner* — Jason M Ip
(74) *Attorney, Agent, or Firm* — Li & Cai Intellectual Property Office

(57) ABSTRACT

An adjustable marker reference device for identifying surgical instruments includes a base, an upper cover, a set of connecting rods, markers and a fixing button. The base has a first groove, and the upper cover has a second groove. The set of connecting rods is disposed between the base and the upper cover, and has two movable ends and a pivot point. The fixing button extends through the first groove, the pivot point and the second groove. When the fixing button is pressed, the set of connecting rods can freely bring the pivot point to slide along the first groove and the second groove. When the fixing button is not pressed and the pivot point is fixed at one of default positions, the set of connecting rods is fixed. As the set of connecting rods is fixed, virtual lines between any two of the markers meet specific conditions.

15 Claims, 14 Drawing Sheets

ADJUSTABLE MARKER REFERENCE DEVICE

CROSS-REFERENCE TO RELATED PATENT APPLICATION

This application claims the benefit of priority to Taiwan Patent Application No. 112138833, filed on Oct. 12, 2023. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a device, and more particularly to an adjustable marker reference device suitable for identifying surgical instruments.

BACKGROUND OF THE DISCLOSURE

Most navigation systems for spinal surgery available on the market typically utilize NDI's (Northern Digital Incorporation) optical identification systems as their foundational positioning mechanism. To enhance the identification process of these optical systems, a variety of surgical navigation instruments are integrated with diverse dynamic reference frames (DRFs).

In practical applications, such as spinal fusion surgery, a variety of surgical instruments including drills, cannulas, K-wires, trocars, taps, and screwdrivers may be utilized. When these tools are integrated with the navigation system, an equivalent number of DRFs with different styles should be designed and produced to represent different functional surgical instruments.

When a multitude of surgical instruments are employed, it necessitates the use of a significant number of the DRFs, which in turn escalates both production and maintenance costs. Furthermore, if a DRF shortage occurs during surgery and a DRF transfer is necessary, the act of transferring these DRFs can not only potentially heighten the risk of contamination, but also diminish the overall success rate of the surgical procedure.

SUMMARY OF THE DISCLOSURE

In response to the above-referenced technical inadequacies, the present disclosure provides an adjustable marker reference device suitable for identifying surgical instruments.

In order to solve the above-mentioned problems, one of the technical aspects adopted by the present disclosure is to provide an adjustable marker reference device, which is suitable for identifying a surgical instrument and includes a base, an upper cover, a set of connecting rods, a plurality of markers and a fixing button. The base is provided with a first groove. The upper cover is disposed on the base and is provided with a second groove corresponding to the first groove. The set of connecting rods is disposed between the base and the upper cover, and has two movable ends and a pivot point. The markers are respectively disposed on the upper cover and the two movable ends. The fixing button extends through the first groove, the pivot point and the second groove. When the fixing button is pressed, the set of connecting rods can freely bring the pivot point to slide along the first groove and the second groove, and when the fixing button is not pressed and the pivot point is located and fixed at one of a plurality of default positions defined by the first groove and the second groove. When the set of connecting rods is fixed, a plurality of virtual lines between any two of the plurality of markers meet the following conditions: lengths of the virtual lines are all greater than a first predetermined length; and a length difference between any two of the virtual lines is greater than a second predetermined length or an angle between any two of the virtual lines is greater than a predetermined angle.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
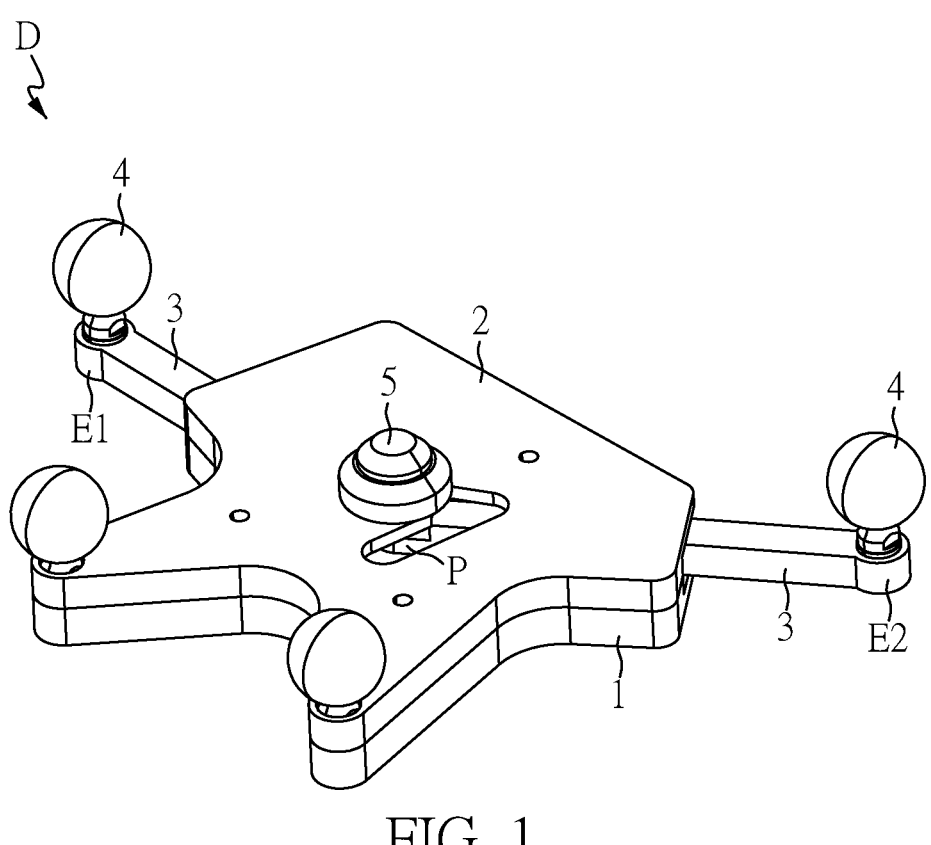
FIG. 1 is a schematic perspective diagram of an adjustable marker reference device according to one embodiment of the present disclosure.
Figure 2:
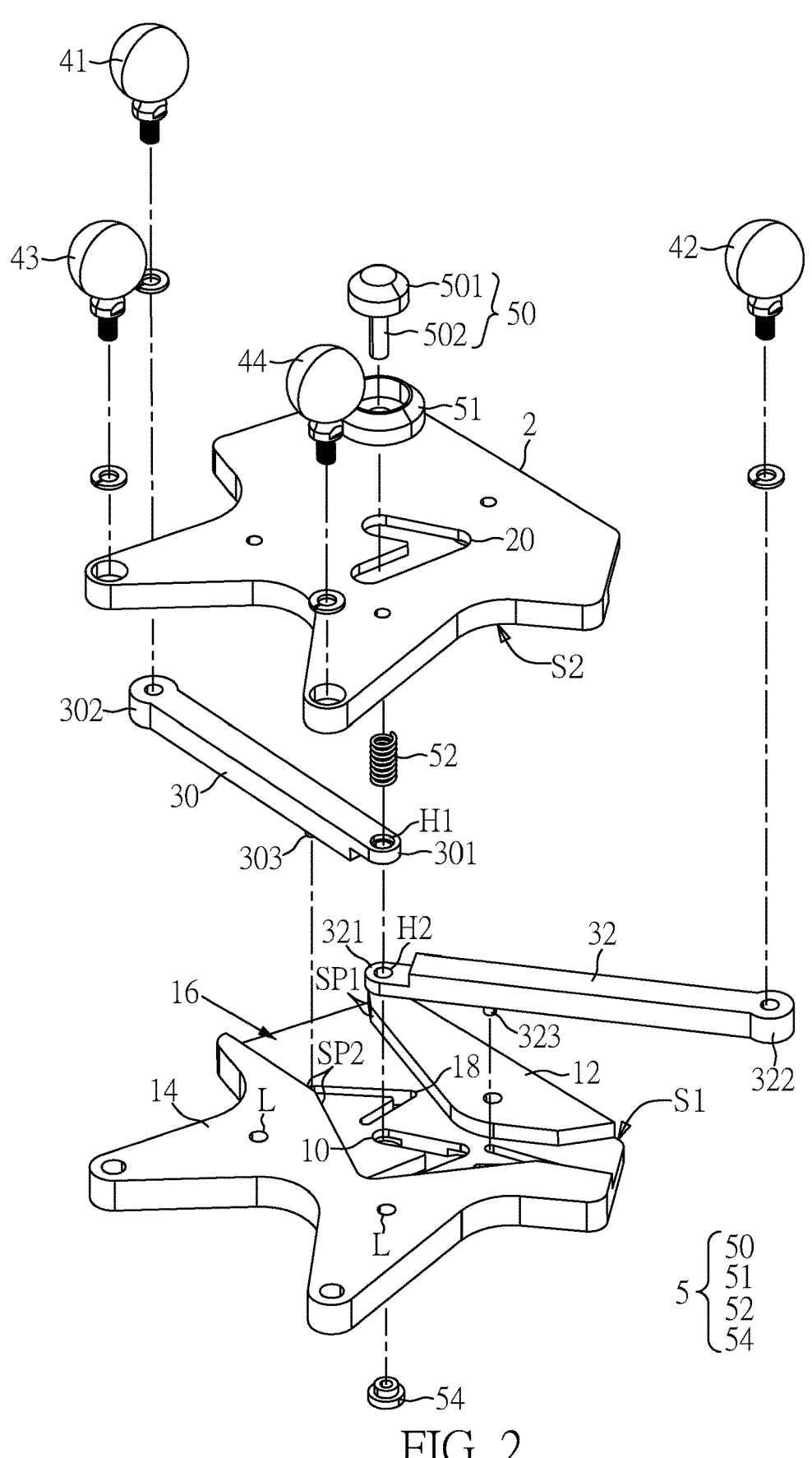
FIG. 2 is an exploded schematic diagram of the adjustable marker reference device according to one embodiment of the present disclosure.
Figure 3:
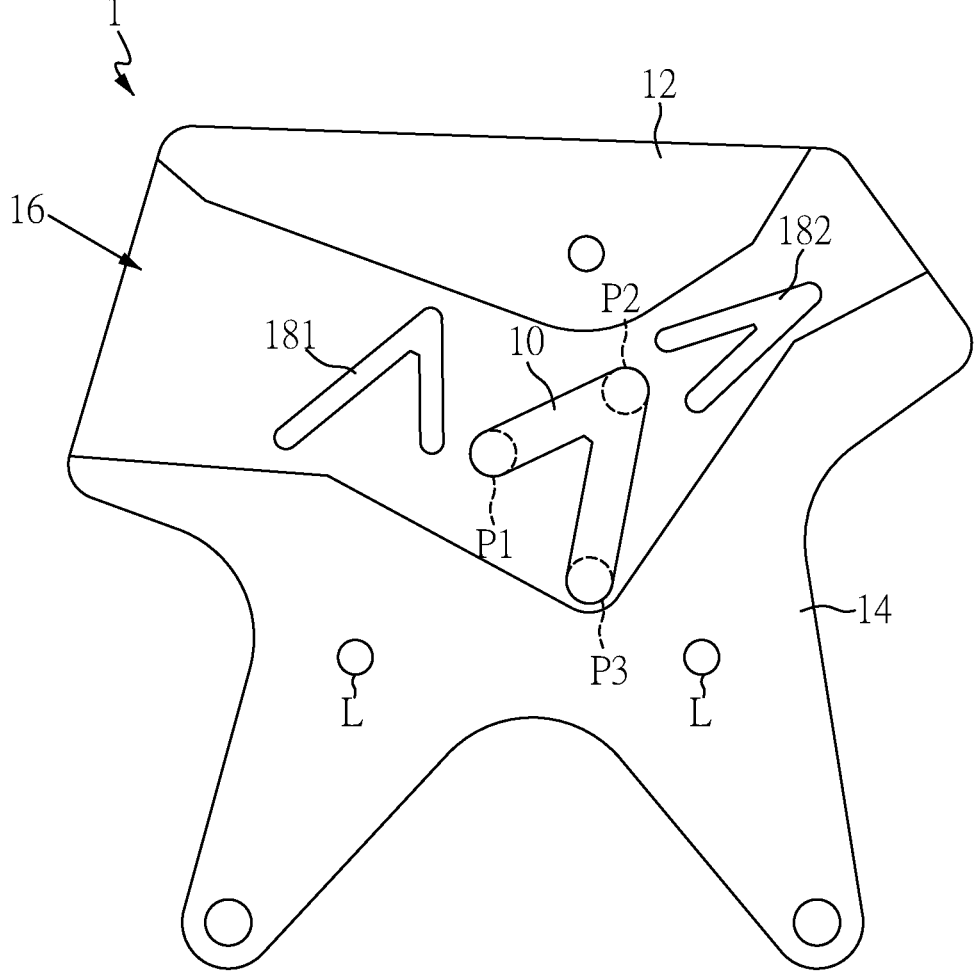
FIG. 3 is a schematic top view of a base of the adjustable marker reference device according to one embodiment of the present disclosure.
Figure 4:
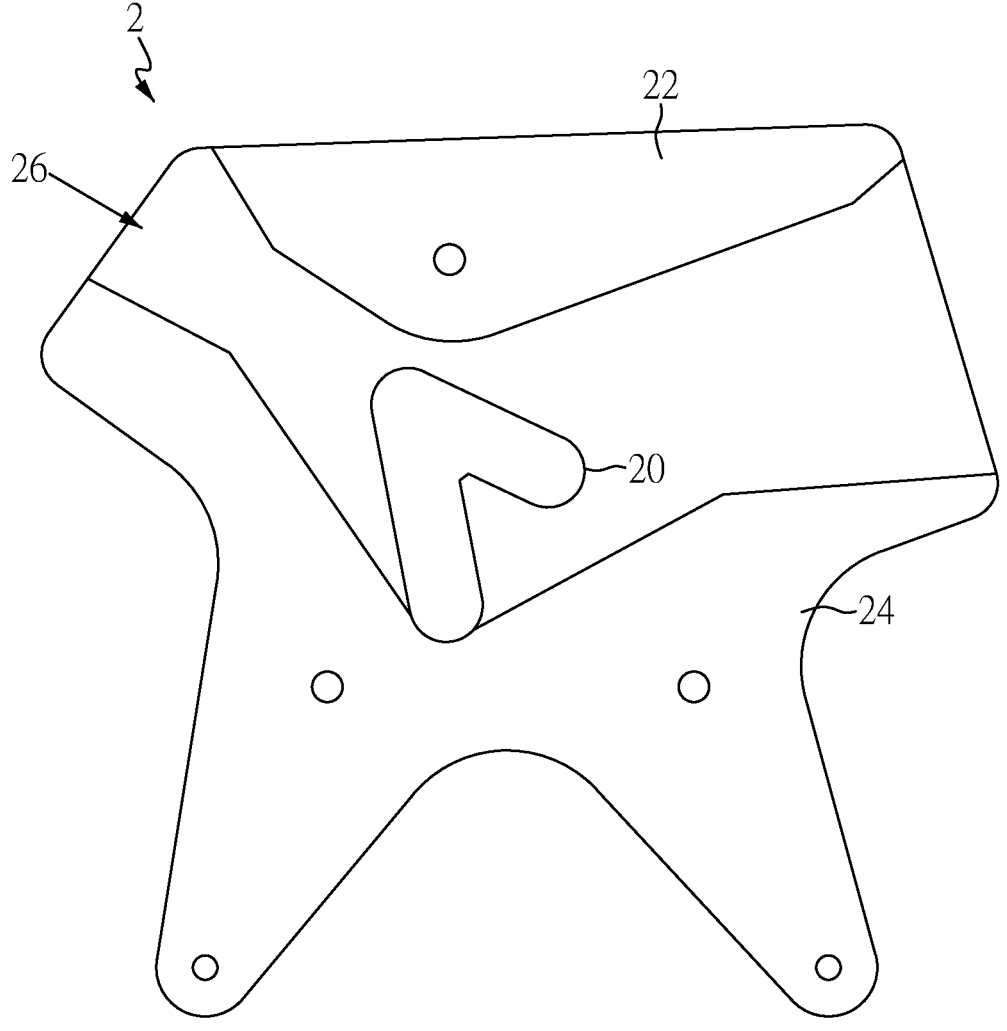
FIG. 4 is a schematic bottom view of an upper cover of the adjustable marker reference device according to one embodiment of the present disclosure.
Figure 5:
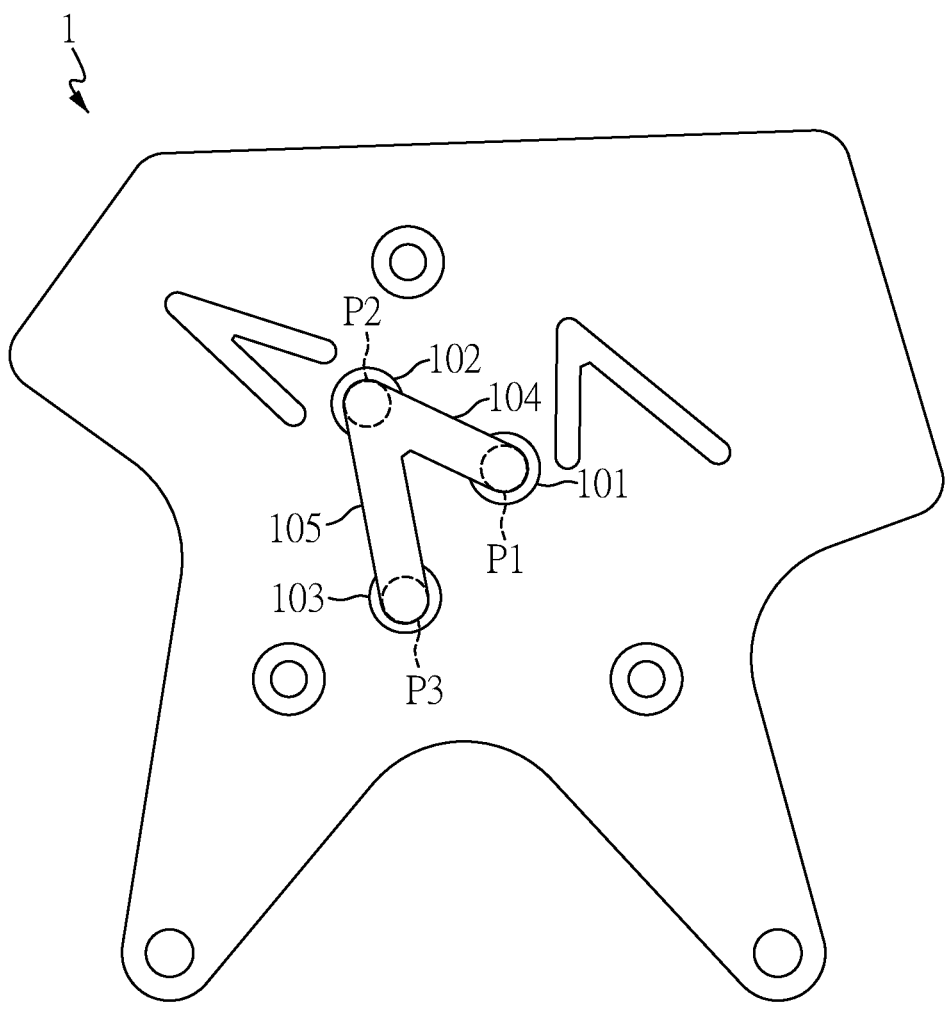
FIG. 5 is a schematic bottom view of the base of the adjustable marker reference device according to one embodiment of the present disclosure.

FIG. 1 is a schematic perspective diagram of an adjustable marker reference device according to one embodiment of the present disclosure, FIG. 2 is an exploded schematic diagram of the adjustable marker reference device according to one embodiment of the present disclosure, FIG. 3 is a schematic top view of a base of the adjustable marker reference device according to one embodiment of the present disclosure, FIG. 4 is a schematic bottom view of an upper cover of the adjustable marker reference device according to one embodiment of the present disclosure, and FIG. 5 is a schematic bottom view of the base of the adjustable marker reference device according to one embodiment of the present disclosure.

Reference is made to FIGS. 1 to 5, a first embodiment of the present disclosure provides an adjustable marker reference device D, which is suitable for identifying surgical instruments and includes a base 1, an upper cover 2, a set of connecting rods 3, a plurality of markers 4 and a fixing button 5.

The base 1 can be, for example, a rigid plate as shown in FIG. 2, with a first groove 10 provided on an upper surface S1 of the base 1. The upper surface S1 of the base 1 is also provided with a first protrusion block 12 and a second protrusion block 14. The main recess portion 16 is formed between the first protrusion block 12 and the second protrusion block 14. The first groove 10 is provided at a bottom of the main recess portion 16.

From the top view, it can be seen that the first protrusion block 12 can have a triangular-hill shape and have a plurality of first positioning surfaces SP1 facing the main recess portion 16. The second protrusion block 14 can have a shape similar to the capital letter H, and an upper half of the letter H forms a plurality of second positioning surfaces SP2 facing the main recess portion 16. The first positioning surfaces SP1 and the second positioning surfaces SP2 are perpendicular to the upper surface S1 of the base 1.

The upper cover 2 is disposed on the base 1 and has a second groove 20 corresponding to the first groove 10. In some embodiments, the upper cover 2 has the same shape as the base 1 (from the top view), and the shape is similar to the shape of the capital letter H. A third protrusion block 22, a fourth protrusion block 24 and a main recess portion 26 can be formed on a lower surface S2 of the upper cover 2 to respectively correspond to the first protrusion block 12, the second protrusion block 14 and the main recess portion 16, so as to provide more space for the set of connecting rods 3 when the upper case 2 is combined with the base 1, thereby allowing the set of connecting rods 3 to use rods with large thicknesses.

The set of connecting rods 3 is arranged between the base 1 and the upper cover 2, especially in the main recess portions 16 and 26, and has two movable ends E1, E2 and a pivot point P. Specifically, with reference to FIG. 2, the set of connecting rods 3 includes a first rod 30 and a second rod 32 disposed in the main recess portion 16. One end 301 of the first rod 30 is connected to one end 321 of the second rod 32 to serve as the pivot point P, and the other end 302 of the first rod 30 and the other end 322 of the second rod 32 serve as the movable ends E1, E2, respectively. As shown in FIG. 2, a first fixing hole H1 is formed at the end 301 that is connected to the second rod 32, and a second fixing hole H2 is formed at the end 321 that is connected to the first rod 30. The end 301 of the first rod 30 and the end 321 of the second rod 32 can have complementary stepped structures, such that the pivot point P can be formed for the fixing button 5 to pass therethrough after the ends 301 and 321 are connected to each other.

In some embodiments, at least one auxiliary groove 18 can be further disposed at a bottom of the main recess portion 16. For example, a quantity of the auxiliary grooves 18 can be two, and the auxiliary grooves 18 include a first auxiliary groove 181 and a second auxiliary groove 182 that are arranged at the bottom of the main recess portion 16. However, the present disclosure is not limited thereto. In the embodiment that the auxiliary grooves are provided, a first positioning pin 303 can be correspondingly arranged on a surface of the first rod 30 facing the base 1, and a second positioning pin 323 can be correspondingly arranged on a surface of the second rod 32 facing the base 1. Thereby, the first auxiliary groove 181 can be used to assist in positioning the first positioning pin 303, and the second auxiliary groove 182 can be used to assist in positioning the second positioning pin 323.

As shown in FIG. 1, the plurality of markers 4 can be respectively disposed on the upper cover 2 and the two movable ends E1, E2 of the set of connecting rods 3, and can be, for example, reflective balls. For example, a quantity of the markers 4 can be four. As shown in FIG. 2, a first marker 41 is connected to the end 302 of the first rod 30, and a second marker 42 is connected to the end 322 of the second rod 32. A third marker 43 and a fourth marker 44 are disposed on the upper cover 2, for example, on two outwardly extending ends of the lower half of the capital letter H. The upper cover 2 and the base 1 are fixed to each other by locking screws (not shown) at a plurality of threaded holes L on the first protrusion block 12, the second protrusion block 14, the third protrusion block 22 and the fourth protrusion block 24. The first marker 41, the second marker 42, the third marker 43 and the fourth marker 44 can be provided with metric screws, and positions on the ends 302, 322 and positions on the upper cover 2 where the markers 43, 44 will be arranged can be provided with corresponding threaded holes for interlocking the markers, the rods and the upper cover. The present disclosure does not limit the manner in which these markers 4 are disposed.

Referring to FIG. 2 again, the fixing button 5 passes through the first groove 10, the pivot point P and the second groove 20. The fixing button 5 includes a button body 50, an elastic member 52 and a bottom fixing pin 54. The button body 50 has a pressing part 501 and a connecting post 502 opposite to the pressing part 501. The elastic member 52 can be, for example, a spring or a similar element, and is disposed between the set of connecting rods 3 and the upper cover 2. The bottom fixing pin 54 is connected to a distal end of the connecting post 502.

The fixing button 5 passes through the first groove 10, the pivot point P and the second groove 20 by extending into the first fixing hole H1 and the second fixing hole H1, so as to fix the first rod 30 and the second rod 32 between the base 1 and the upper cover 2. The connecting post 502 passes through the second groove 20, the elastic member 52, the first fixing hole H1, the second fixing hole H2 and the first groove 10, and is connected to the bottom fixing pin 54.

In some embodiments, the fixing button 5 can further include a supporting sleeve member 51, which has a groove for receiving the button body 50, and a through hole is formed at a bottom of the groove for the connecting post 502 to pass through, thereby increasing stability when the button body 50 is pressed.

Therefore, when the fixing button 5 is pressed, the set of connecting rods 3 can freely bring the pivot point P to slide along the first groove 10 and the second groove 20, and each of the first groove 10 and the second groove 20 has at least three anchoring positions. When the fixing button 5 is not pressed and the pivot point P is located at one of default positions P1, P2 and P3 defined by the first groove 10 and the second groove 20, the set of connecting rods 3 is fixed.

For example, when the pivot point P is located at the default position P1, P2 or P3 and the set of connecting rods 3 is fixed, at least one of the first positioning surfaces SP1 and at least one of the second positioning surfaces SP2 abut against the set of connecting rods 3. Through these three anchoring positions, the markers 4 can have at least three configuration relationships when the set of connecting rods 3 is fixed. Each of the configuration relationships corresponds to one of the default positions P1, P2, P3 where the set of connecting rods 3 can be located. However, the present disclosure is not limited thereto.

For example, as can be seen from FIG. 5, the first groove 10 is provided with fixing grooves 101, 102 and 103 corresponding to the bottom fixing pin 54 at the default positions P1, P2 and P3. The fixing grooves 101 can be connected to the fixing groove 102 through a track groove 104, and the fixing groove 102 can be connected to the fixing groove 103 through the track groove 105. It should be noted that shapes of the fixing grooves 101, 102, 103 are circular grooves when viewed from below, and diameters of the circular grooves are slightly larger than a diameter of the bottom fixing pin 54, so as to allow the bottom fixing pin 54 to pass through the fixing grooves 101, 102, 103 when the fixing button 5 is pressed. On the other hand, widths of the track grooves 104 and 105 can be slightly larger than a diameter of the connecting post 502 but smaller than the diameter of the bottom fixing pin 54, so to form a securing structure for fixing the fixing button 5 together with the pivot point P (that is, the end 301 of the first rod 30 and the end 321 of the second rod 32) at the default positions P1, P2, and P3 when the bottom fixing pin 54 is located in the fixing grooves 101, 102, 103, thereby forming the so-called anchoring positions.

It should be noted that similar to the first groove 10 and the second groove 20, the first auxiliary groove 181 and the second auxiliary groove 182 also have at least three anchoring parts each, and the first groove 10, the second groove 20, the first auxiliary groove 181, and the second auxiliary groove 182 are not only similar in shape (for example, all are V-shaped), but the various anchoring positions therein are also highly correlated in respect to their locations.

Figure 6:
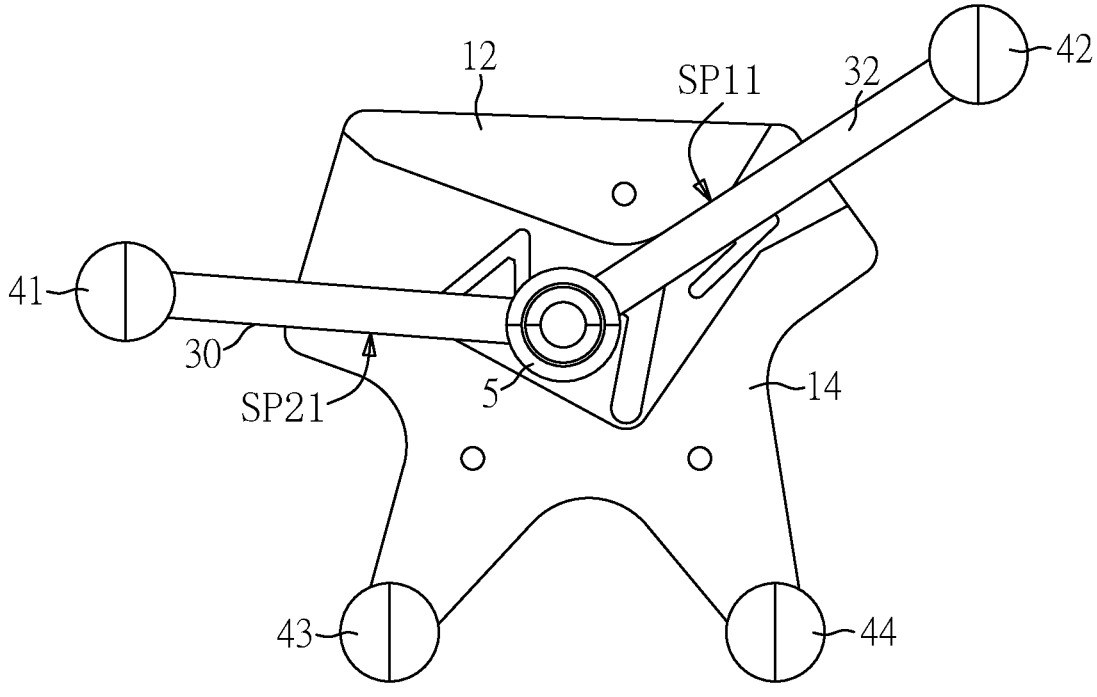
FIG. 6 is a schematic top view of a first configuration relationship of the adjustable marker reference device according to one embodiment of the present disclosure.

Reference is made to FIG. 6, which is a schematic top view of a first configuration relationship of the adjustable marker reference device according to one embodiment of the present disclosure. In FIG. 6, the upper cover 2 is omitted for the convenience of explaining the positional relationship of the first marker 41, the second marker 42, the third marker 43, the fourth marker 44, the first rod 30, and the second rod 32 relative to the base 1. In the first configuration relationship, one surface of the first rod 30 facing the second protrusion block 14 abuts against the positioning surface SP21 of the second protrusion portion 14, a joint portion (i.e., the pivot point P) between the first rod 30 and the second rod 32 is also fixed at the default position P1 in FIG. 5 along with the fixing button 5, and a surface of the second rod 32 facing the first protrusion block 12 abuts against the positioning surface SP11 of the first protrusion block 12. Through setup of the positioning surface SP11, positioning surface SP21, the first auxiliary groove 181, the second auxiliary groove 182, and the fixing groove 101, the first rod 30 and the second rod 32 can be firmly supported under various operating conditions without changing the relative positional relationship of the first marker 41, the second marker 42, the third marker 43, and the fourth marker 44.

Figure 7:
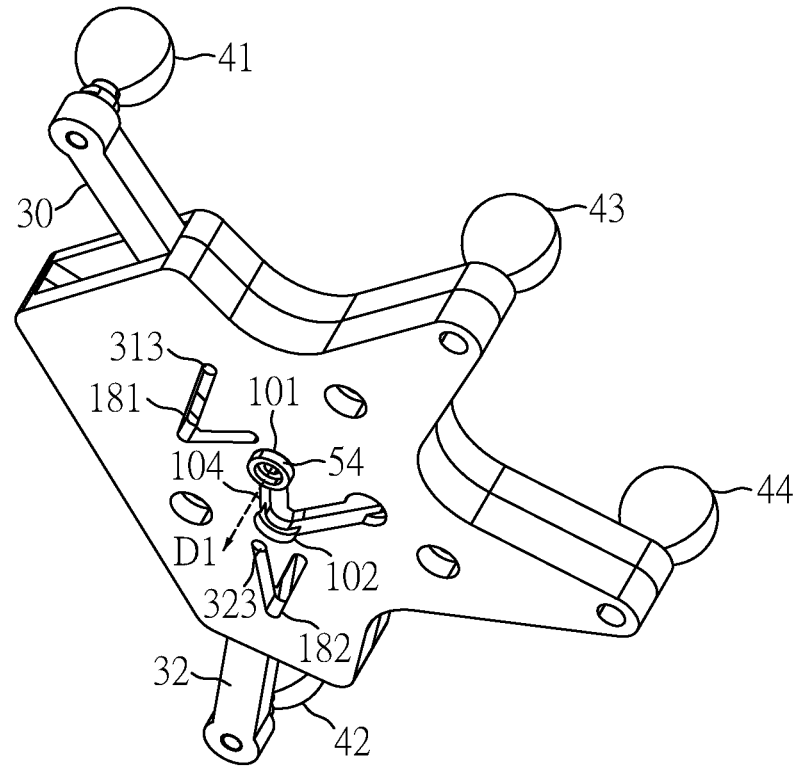
FIG. 7 is a schematic diagram showing a fixing button of the adjustable marker reference device that is pressed according to one embodiment of the present disclosure.

Reference can be made to FIG. 7, which is a schematic diagram showing that a fixing button of the adjustable marker reference device is pressed according to one embodiment of the present disclosure. The first positioning pin 313 is positioned at one end of the V-shaped portion with the assistance of the first auxiliary groove 181, and the second positioning pin 323 is positioned at one end of the V-shaped portion with the assistance of the second auxiliary groove 182. Specifically, when the bottom fixing pin 54 is located in a current one of the fixing grooves (for example, the fixing groove 101) and the button body 50 is pressed, the bottom fixing pin 54 can move from the fixing groove 101 in a direction D1 shown in FIG. 7, allowing the connecting post 502 of the button body 50 to move from the current fixing groove 101 along the track groove 104 to another fixing groove 102, and at the same time the markers 4 are allowed to switch from a current one of the configuration relationships to another one of the configuration relationships. When the button body 50 is pressed, one end of the elastic member 52 abuts against a part of the set of connecting rods 3 and is in a compressed state, and the connecting post 502 of the button body 50 can bring the bottom fixing pin 54 to move outward away from the fixing groove 101.

Figure 8:
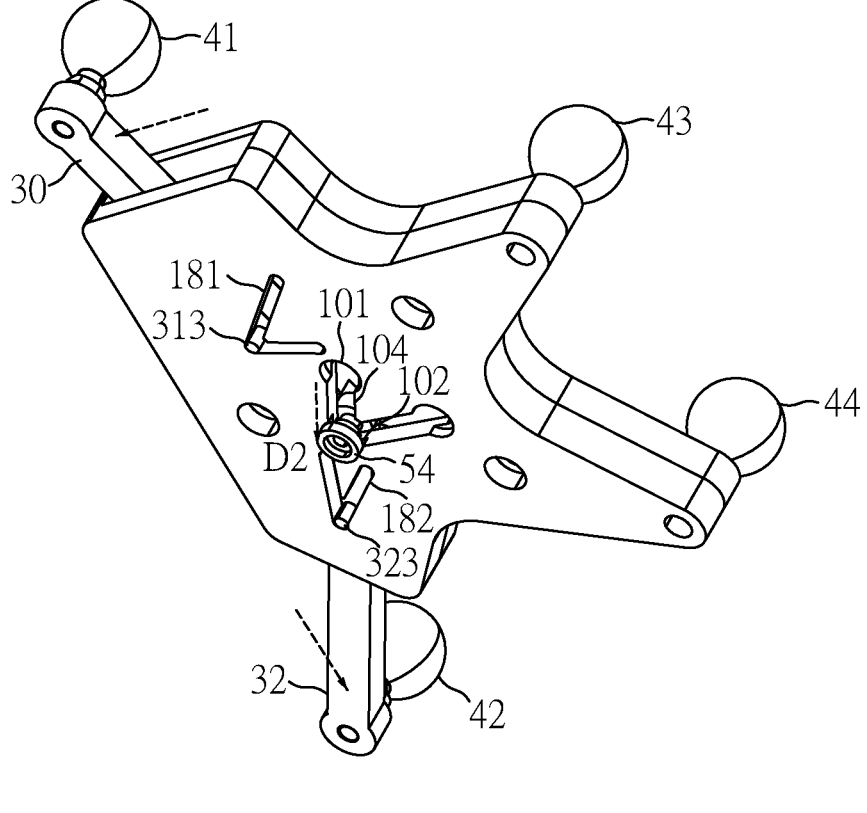
FIG. 8 is a schematic diagram showing the fixing button of the adjustable marker reference device being moved to another default position according to one embodiment of the present disclosure.
Figure 9:
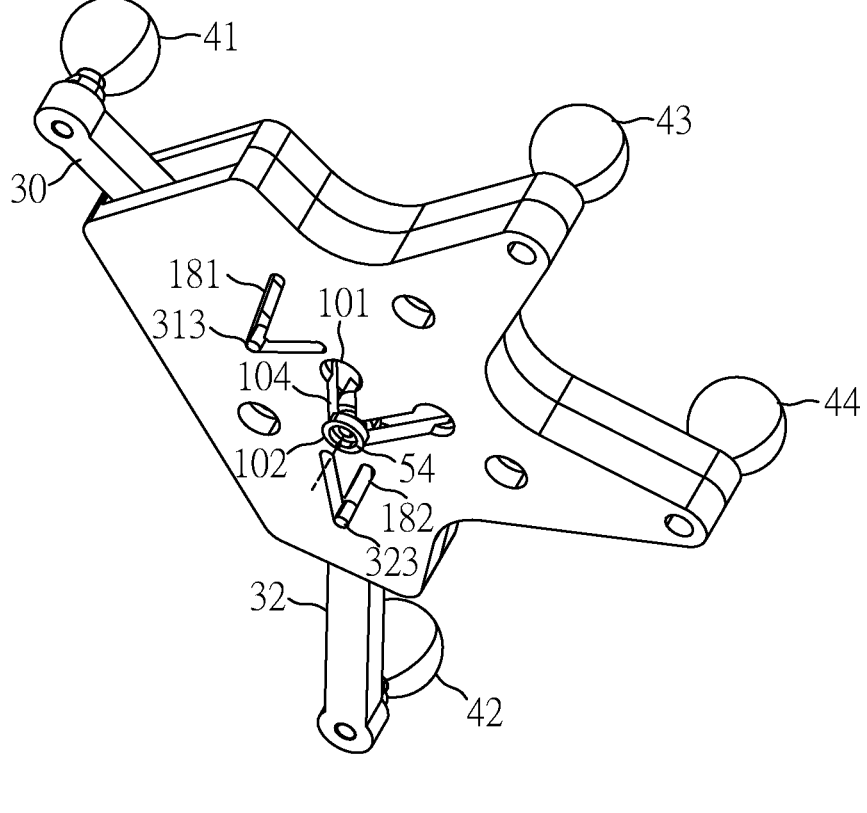
FIG. 9 is a schematic diagram showing the fixing button of the adjustable marker reference device being released according to one embodiment of the present disclosure.

Reference is made to FIGS. 8 and 9. FIG. 8 is a schematic diagram showing the fixing button of the adjustable marker reference device being moved to another default position according to one embodiment of the present disclosure, and FIG. 9 is a schematic diagram showing the fixing button of the adjustable marker reference device being released according to one embodiment of the present disclosure. When the connecting post 502 of the button body 50 moves from the current fixing groove 101 along the track groove 104 (i.e., a direction D2) to another fixing groove 102, with the first rod 30 and the second rod 32 being driven, the first positioning pin 313 moves from one end of the first auxiliary groove 181 to a turning point of the V-shaped portion, and the second positioning pin 323 also moves from one end of the second auxiliary groove 182 to a turning point of the V-shaped portion.

Then, when the button body 50 is no longer pressed (i.e., being released) as shown in FIG. 9, the bottom fixing pin 54 is allowed to enter the fixing groove 102, which fixes the set of connecting rods 3, and at the same time allows the markers 4 to complete a switch to another configuration relationship. When the button body 50 is released, the elastic member 52 returns to a non-compressed state, and the other end of the elastic member 52 pushes against the button body 50, such that the connecting post 502 drives the bottom fixing pin 54 back to the fixing groove 102.

Figure 10:
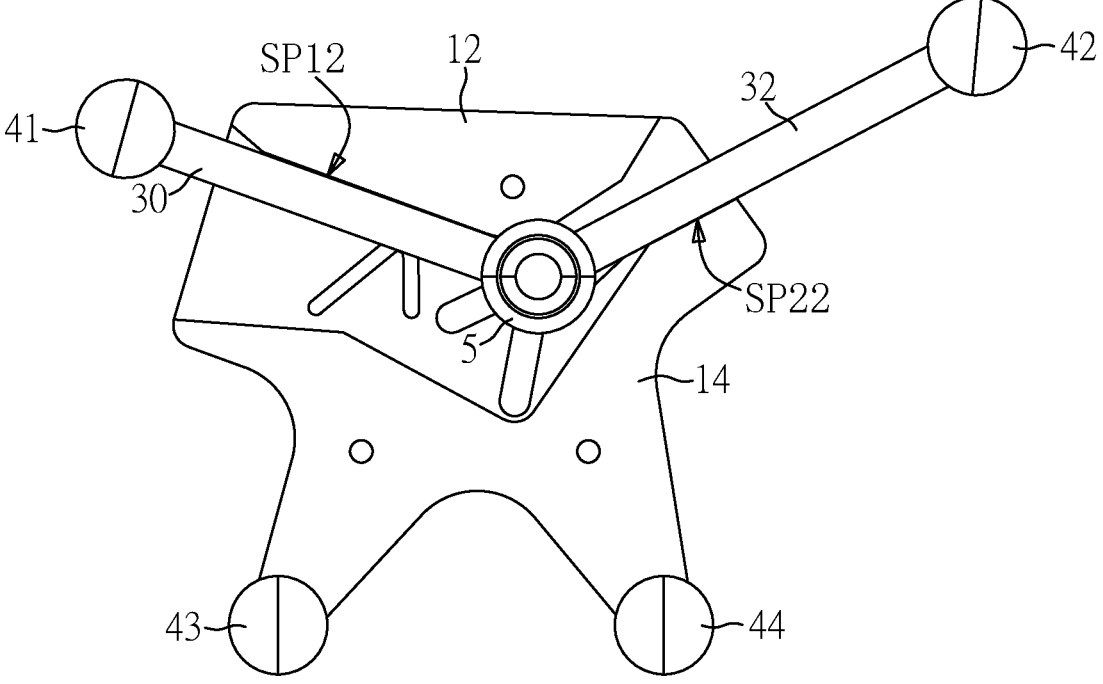
FIG. 10 is a schematic top view of a second configuration relationship of the adjustable marker reference device according to one embodiment of the present disclosure.

Reference is made to FIG. 10, which is a schematic top view of a second configuration relationship of the adjustable marker reference device according to one embodiment of the present disclosure. In FIG. 10, the upper cover 2 is omitted for convenience of explanation. In the second configuration relationship, the surface of the first rod 30 facing the first protrusion block 12 abuts against the positioning surface SP12 of the first protrusion block 12, and the joint portion (i.e., the pivot point P) between the first rod 30 and the second rod 32 is fixed at the default position P2 along with the fixing button 5. In addition, the surface of the second rod 32 facing the second protrusion block 14 abuts against the positioning surface SP22 of the second protrusion block 14. Through setup of the positioning surface SP12, the positioning surface SP22, the first auxiliary groove 181, the second auxiliary groove 182, and the fixing groove 102, the first rod 30 and the second rod 32 can be firmly supported under various operating conditions without changing the relative positional relationship of the first marker 41, the second marker 42, the third marker 43, and the fourth marker 44.

Figure 11:
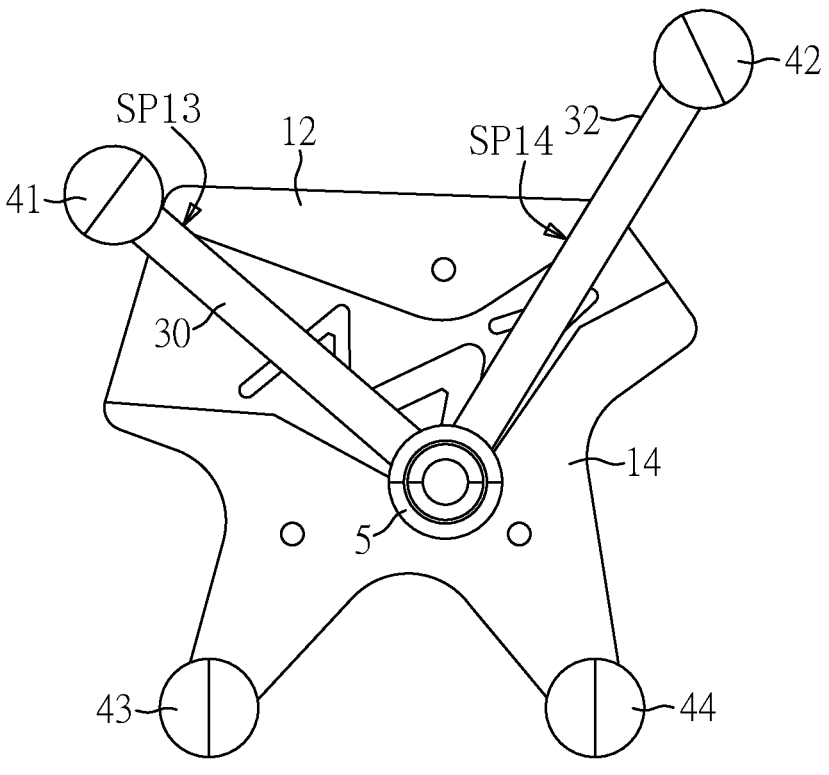
FIG. 11 is a schematic top view of a third configuration relationship of the adjustable marker reference device according to one embodiment of the present disclosure.

Reference is made to FIG. 11, which is a schematic top view of a third configuration relationship of the adjustable marker reference device according to one embodiment of the present disclosure. Similar to the aforementioned operation, under the second configuration relationship, the button body 50 can be pressed to make the bottom fixing pin 54 leave the fixing groove 102 and push the button body 50, such that the connecting post 502 can move from the current fixing groove 102 along the track groove 105 to another fixing groove 103, after which the fixing button 5 is released to allow the bottom fixing pin 54 to enter the fixing groove 103, thereby switching from the second configuration relationship to the third configuration relationship.

In FIG. 11, the upper cover 2 is omitted for convenience of explanation. In the third configuration relationship, the surface of the first rod 30 facing the first protrusion block 12 abuts against the positioning surface SP13 of the first protrusion block 12, and the joint portion (i.e., the pivot point P) between the first rod 30 and the second rod 32 is fixed at the default position P3 along with the fixing button 5. In addition, the surface of the second rod 32 facing the first protrusion block 12 abuts against the positioning surface SP14 of the first protrusion block 12. Through setup of the positioning surface SP13, positioning surface SP14, the first auxiliary groove 181, the second auxiliary groove 182, and the fixing groove 103, the first rod 30 and the second rod 32 can be firmly supported under various operating conditions without changing the relative positional relationship of the first marker 41, the second marker 42, the third marker 43, and the fourth marker 44.

It should be noted that when the set of connecting rods 3 is fixed, a plurality of virtual lines between any two of the markers 4 meet certain conditions, such that an optical system can identify different surgical instruments according to the above-mentioned first to third configuration relationships. In the following, embodiments will be recited based on taking the optical recognition system from NORTHERN DIGITAL INC. (NDI) as a positioning reference. Different types of surgical instruments used in navigational surgery need to be combined with different dynamic reference frames (DRFs) for recognition by the optical system.

A design of DRF is based on a principle of arranging the aforementioned markers 4 (for example, reflective balls) in the same plane, and an arrangement of the markers 4 must comply with NDI's DRF design rules (for example, Polaris Tool Design Guide 10005896 R02), including the following conditions:

Condition 1: lengths of the virtual line are greater than a first predetermined length;

Condition 2: a length difference between any two of the virtual lines is greater than a second predetermined length; and Condition 3: an angle between any two of the virtual lines is greater than a predetermined angle.

Condition 1 is a required condition, and only one of condition 2 and condition 3 needs to be met. In other words, if the length difference between two of the virtual lines is less than the second predetermined length, then the angle between the two virtual lines needs to be greater than the predetermined angle. On the contrary, if the angle between the two virtual lines is less than the predetermined angle, the length difference between the two virtual lines needs to be greater than the second predetermined length.

In the present embodiment, the first predetermined length ranges from 30 mm to 60 mm, the second predetermined length ranges from 2 mm to 5 mm, and the predetermined angle ranges from 1 degrees to 5 degrees. In a preferred embodiment, for more precise identification, the first predetermined length ranges from 45 mm to 55 mm, e.g., 50 mm, the second predetermined length ranges from 3 mm to 4 mm, e.g., 3.5 mm, and the predetermined angle ranges from 3 degrees to 4 degrees, e.g., 2 degrees.

Figure 12:
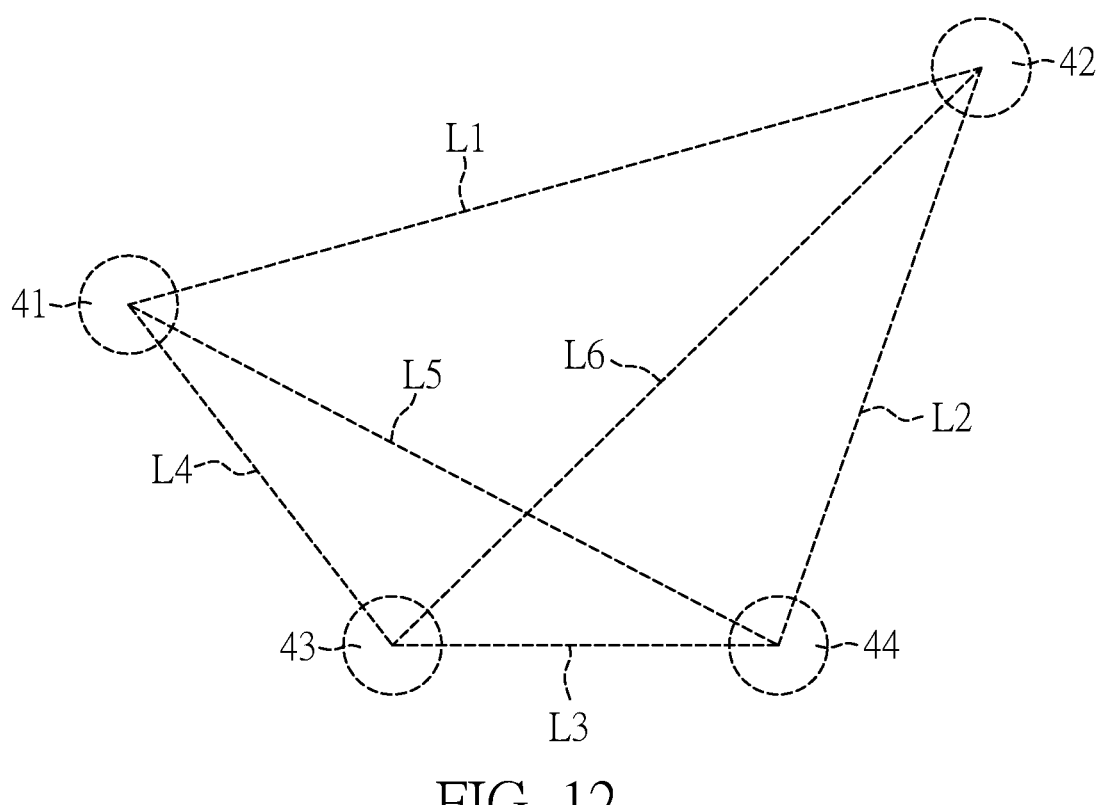
FIGS. 12, 13 and 14 are respectively schematic diagrams of virtual lines between any two of the markers in the first, second and third configuration relationships according to one embodiment of the present disclosure.
Figure 13:
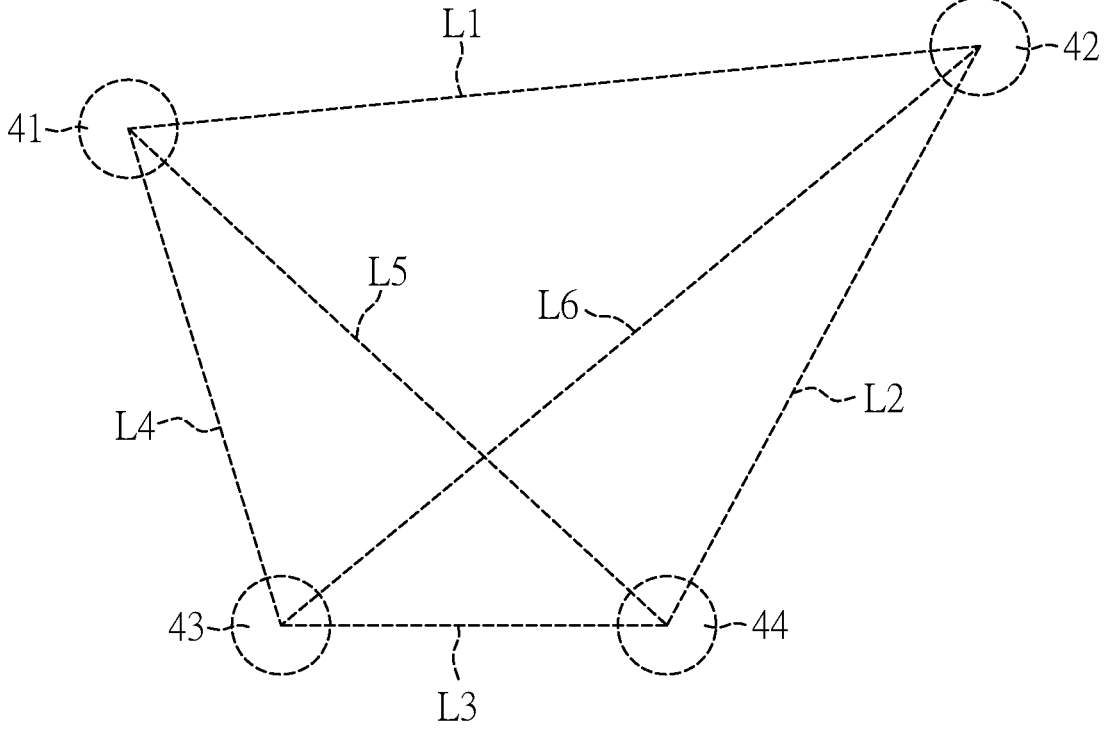
Figure 14:
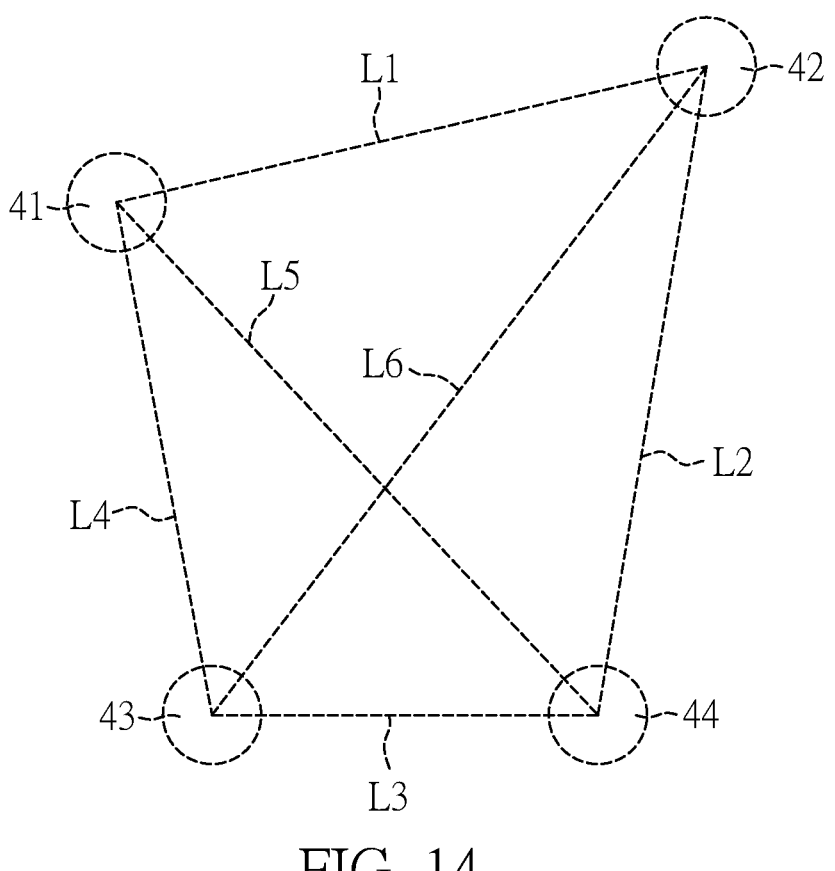

Reference is made to FIGS. 12, 13 and 14. FIGS. 12, 13 and 14 are respectively schematic diagrams of virtual lines between any two of the markers in the first, second and third configuration relationships according to one embodiment of the present disclosure. According to the first configuration relationship shown in FIG. 6, the markers 41, 42, 43, and 44, along with virtual lines L1, L2, L3, L4, L5, and L6, can be drawn as shown in FIG. 12. Specifically, the virtual line L1 is formed by connecting the first marker 41 to the second marker 42, the virtual line L2 is formed by connecting the second marker 42 to the fourth marker 44, the virtual line L3 is formed by connecting the third marker 43 to the fourth marker 44, the virtual line L4 is formed by connecting the first marker 41 to the third marker 43, the virtual line L5 is formed by connecting the first marker 41 to the fourth marker 44, and the virtual line L6 is formed by connecting the second marker 42 to the third marker 43.

In the first configuration relationship, the lengths of the virtual lines L1, L2, L3, L4, L5, and L6 are 117, 81, 51, 57, 97, and 109, respectively (e.g., in millimeters). All the lengths of the virtual lines are greater than the first predetermined length set by condition 1, and the length difference between any two of the virtual lines is greater than the second predetermined length set by condition 2, which therefore complies with the DRF design rules of NDI.

In the second configuration relationship, the lengths of the virtual lines L1, L2, L3, L4, L5, and L6 are 113, 87, 51, 69, 97, and 119, respectively (e.g., in millimeters). All the lengths of the virtual lines are greater than the first predetermined length set by condition 1, and the length difference between any two of the virtual lines is greater than the second predetermined length set by condition 2, which therefore complies with the DRF design rules of NDI.

In the third configuration relationship, the lengths of the virtual lines L1, L2, L3, L4, L5, and L6 are 80, 87, 51, 69, 93, and 108, respectively (e.g., in millimeters). All the lengths of the virtual lines are greater than the first predetermined length set by condition 1, and the length difference between any two of the virtual lines is greater than the second predetermined length set by condition 2, which therefore complies with the DRF design rules of NDI.

Furthermore, to achieve the aforementioned first to third configuration relationships, it is necessary to adapt setup of the first groove 10, the second groove 20, the first auxiliary groove 181, the second auxiliary groove 182, and the set of connecting rods 3. Taking the first groove 10 and the corresponding second groove 20 as an example, when three configuration relationships are needed, the first groove 10 can be formed as shown in FIG. 3 by joining two straight grooves in different directions, thereby providing three anchoring positions. According to such an example, the second groove 20, the first auxiliary groove 181, and the second auxiliary groove 182 can be designed to have similar grooves. Conceivably, when four configuration relationships are needed, the first groove 10 can be formed by joining three straight grooves extending in different directions (e.g., lightning-shaped), thereby providing four anchoring positions. By analogy, the configuration of the first groove 10, the second groove 20, the first auxiliary groove 181, the second auxiliary groove 182, and the set of connecting rods 3 can be designed according to a quantity of required configuration relationships. Therefore, a single adjustable marker reference device D can be converted to multiple type DRFs with different configurations.

Furthermore, although not specifically illustrated, in the adjustable marker reference device D provided by the present disclosure, the surgical instrument can be fixed to the surface of the base 1 or the upper cover 2 that does not face the set of connecting rods 3, and the present disclosure does not limit the manner for fixing the adjustable marker reference device D and the surgical instrument. For example, after combining with the surgical instrument through an adapter that fits an outer shape of the surgical instrument, the adjustable marker reference device D can be used to allow the optical identification system to identify the surgical instrument connected thereto.

Beneficial Effects of the Embodiments

In conclusion, the disclosed adjustable marker reference device can convert to multiple different DRF configurations, so that users only need to set different configurations for surgical instruments to be used. It is unnecessary to prepare a large number of DRFs with different configurations, which effectively reduces a quantity of DRF devices required for an operation.

Furthermore, through the configuration of the positioning surfaces, the auxiliary grooves, and the fixing grooves, the set of connecting rods can be stably supported in various operating situations without changing relative positions of the markers. Moreover, all configurations comply with DRF design rules of NDI.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching. The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. An adjustable marker reference device, for use in identifying a surgical instrument, the adjustable marker reference device comprising:
  a base provided with a first groove;
  an upper cover disposed on the base, wherein the upper cover is provided with a second groove corresponding to the first groove;
  a set of connecting rods disposed between the base and the upper cover, wherein the set of connecting rods has two movable ends and a pivot point;

a plurality of markers respectively disposed on the upper cover and the two movable ends;
  a fixing button extending through the first groove, the pivot point and the second groove, wherein, when the fixing button is pressed, the set of connecting rods is capable of freely bringing the pivot point to slide along the first groove and the second groove, and when the fixing button is not pressed and the pivot point is located and fixed at one of a plurality of default positions defined by the first groove and the second groove, the set of connecting rods is fixed;
  wherein, when the set of connecting rods is fixed, a plurality of virtual lines between any two of the plurality of markers meet the following conditions:
  lengths of the virtual lines are all greater than a first predetermined length; and
  a length difference between any two of the virtual lines is greater than a second predetermined length, or an angle between any two of the virtual lines is greater than a predetermined angle.

2. The adjustable marker reference device according to claim 1, wherein the first groove and the second groove each have at least three anchoring positions, such that the plurality of markers have at least three configuration relationships, each of the configuration relationships corresponds to one of the default positions.

3. The adjustable marker reference device according to claim 2, wherein the base has a first protrusion block and a second protrusion block, a main recess portion is formed between the first protrusion block and the second protrusion block, and the first groove and at least one auxiliary groove are provided at a bottom of the main recess portion.

4. The adjustable marker reference device according to claim 3, wherein the set of connecting rods includes a first rod and a second rod that are disposed in the main recess portion, one end of the first rod connects with one end of the second rod to form a pivot point, and the other end of the first rod and the other end of the second rod respectively form the movable ends.

5. The adjustable marker reference device according to claim 4, wherein the first rod has a first positioning pin, and the second rod has a second positioning pin, and the at least one auxiliary groove includes a first auxiliary groove and a second auxiliary groove, the first auxiliary groove is used for positioning the first positioning pin, the second auxiliary groove is used for positioning the second positioning pin.

6. The adjustable marker reference device according to claim 4, wherein the first protrusion block has a plurality of first positioning surfaces facing the main recess portion, and the second protrusion block has a plurality of second positioning surfaces facing the main recess portion.

7. The adjustable marker reference device according to claim 6, wherein, when the pivot point is located at one of the default positions and the set of connecting rods is fixed, at least one of the first positioning surfaces and at least one of the second positioning surfaces abut against the set of connecting rods.

8. The adjustable marker reference device according to claim 4, wherein the first rod has a first fixing hole at the end where the first rod connects with the second rod, the second rod has a second fixing hole at the end where the second rod connects with the first rod, and the fixing button passing through the first fixing hole and the second fixing hole is used for extending through the first groove, the pivot point and the second groove, so as to fix the first rod and the second rod between the base and the upper cover.

9. The adjustable marker reference device according to claim 8, wherein the fixing button includes:

a button body having a pressing part and a connecting post opposite to the pressing part;

an elastic member disposed between the set of connecting rods and the upper cover; and a bottom fixing pin connected to a distal end of the connecting post, wherein the connecting post penetrates through the second groove, the elastic member, the first fixing hole, the second fixing hole and the first groove, for being connected to the bottom fixing pin.

10. The adjustable marker reference device according to claim 9, wherein the first groove is provided with a plurality of fixing grooves at the default positions at which the bottom fixing pin respectively corresponds to one of the fixing grooves, and the fixing grooves are connected in sequence by at least one track groove.

11. The adjustable mark reference device according to claim 10, wherein, when the bottom fixing pin is located in a current one of the fixing grooves and the button body is pressed, the bottom fixing pin leaves the current one of the fixing grooves to allow the connecting post of the button body to move to another one of the fixing grooves along the at least one track groove, and at the same time the plurality of markers are allowed to switch from a current one of the configuration relationships to another one of the configuration relationships; and wherein, when the connecting post of the button body moves to the another one of the fixing groove, and the button body is no longer pressed, the bottom fixing pin is allowed to enter the another one of the fixing groove to fix the set of connecting rods in place, and at the same time the markers are completely switched to the another one of the configuration relationships.

12. The adjustable marker reference device according to claim 11, wherein, when the button body is pressed, one end of the elastic member abuts against a part of the set of connecting rods and the elastic member is in a compressed state, and the connecting post of the button body brings the bottom fixing pin to move away from the fixing groove; and wherein, when the button body is released, the elastic member returns to an non-compressed state, and the other end of the elastic member pushes against the button body, such that the connecting post brings the bottom fixing pin to return to the fixing groove.

13. The adjustable marker reference device according to claim 1, wherein a quantity of the plurality of markers is 4, the first predetermined length ranges from 30 mm to 60 mm, the second predetermined length ranges from 2 mm to 5 mm, and the predetermined angle ranges from 1 degree to 5 degrees.

14. The adjustable marker reference device according to claim 4, wherein the plurality of markers include:

a first marker connected to the other end of the first rod;

a second marker connected to the other end of the second rod; and a third marker and a fourth marker provided on the upper cover.

15. The adjustable marker reference device according to claim 3, wherein the upper cover and the base are fixed to each other by locking a plurality of screws through a plurality of threaded holes located on the first protrusion block and the second protrusion block.

\* \* \* \* \*